(12) United States Patent
Searing et al.

(10) Patent No.: US 12,133,755 B2
(45) Date of Patent: Nov. 5, 2024

(54) X-RAY IMAGE DATA MONITORING AND SIGNALING FOR PATIENT SAFETY

(71) Applicant: BAE SYSTEMS IMAGING SOLUTIONS INC., San Jose, CA (US)

(72) Inventors: Stanley K. Searing, San Jose, CA (US); Kwang Bo Cho, San Jose, CA (US); Hung T. Do, San Jose, CA (US); Stephen W. Mims, San Diego, CA (US); Marc K. Thacher, San Diego, CA (US); Bruce E. Willy, Watsonville, CA (US); Glen L. Collier, Morgan Hill, CA (US); Douglas W. Teeter, Scotts Valley, CA (US); George Y. Wang, San Jose, CA (US)

(73) Assignee: BAE Systems Imaging Solutions Inc., San Jose, CA (US)

( * ) Notice: Subject to any disclaimer, the term of this patent is extended or adjusted under 35 U.S.C. 154(b) by 392 days.

(21) Appl. No.: 17/644,201

(22) Filed: Dec. 14, 2021

(65) Prior Publication Data

US 2023/0181134 A1 Jun. 15, 2023

(51) Int. Cl.
*A61B 6/51* (2024.01)
*A61B 6/00* (2006.01)
(Continued)

(52) U.S. Cl.
CPC ............ *A61B 6/512* (2024.01); *A61B 6/4233* (2013.01); *A61B 6/5258* (2013.01); *A61B 6/54* (2013.01);
(Continued)

(58) Field of Classification Search
CPC ..... A61B 6/512; A61B 6/4233; A61B 6/5258; A61B 6/54; A61B 6/56; A61B 6/4452;
(Continued)

(56) References Cited

U.S. PATENT DOCUMENTS 6,047,043 A * 4/2000 Kamps ..................... H05G 1/64
378/98.12
7,471,768 B2 * 12/2008 Curtis ..................... A61B 6/544
378/98.12

(Continued)

*Primary Examiner* — David P Porta
*Assistant Examiner* — Mamadou Faye
(74) *Attorney, Agent, or Firm* — Gary McFaline (57) ABSTRACT

Techniques are provided for x-ray image data monitoring and signaling for patient safety. A methodology implementing the techniques according to an embodiment includes integrating energy associated with a received x-ray pulse at an array of pixels. The method also includes multiplexing a readout of the integrated energy from the array of pixels, as analog signals, into channels, and performing analog to digital conversion of the analog signals of the channels into digital signals. The method further includes generating an error indicator in response to determining that a calculated mean of the digital signals is either greater than an upper threshold value associated with saturation or less than a lower threshold value associated with underexposure. The method further includes transmitting the error indicator over a Universal Serial Bus, to an imaging system, to terminate transmission of further x-ray pulses.

18 Claims, 8 Drawing Sheets

(51) Int. Cl.
*A61B 6/42* (2024.01)
*G01T 1/17* (2006.01)
*G06T 7/00* (2017.01)

(52) U.S. Cl.
CPC .................. *A61B 6/56* (2013.01); *G01T 1/17* (2013.01); *G06T 7/0012* (2013.01); *G06T 2207/10116* (2013.01); *G06T 2207/30036* (2013.01); *G06T 2207/30168* (2013.01)

(58) Field of Classification Search
CPC ....... A61B 6/542; G01T 1/17; G01T 1/20184; G06T 7/0012; G06T 2207/10116; G06T 2207/30036; G06T 2207/30168; G06T 7/0002
See application file for complete search history.

(56) References Cited

U.S. PATENT DOCUMENTS

| | | | |
|---|---|---|---|
| 2004/0028174 A1* | 2/2004 | Koren | A61B 6/563 705/2 |
| 2012/0236982 A1* | 9/2012 | Star-Lack | A61B 6/032 378/7 |
| 2014/0093039 A1* | 4/2014 | Yang | G01T 1/17 250/394 |
| 2015/0155421 A1* | 6/2015 | Biava | C04B 35/01 438/97 |
| 2016/0212363 A1* | 7/2016 | Kim | G06T 7/13 |

* cited by examiner

Data Quality
Measurement Circuit
350

Digital Pixel
Readouts
390

↓

Pixel Summing
Circuit
400

↓

Background
Subtraction
Circuit
410

↓

Normalization
Circuit
420

↓

Thresholding
Circuit
430

↓

Error
Indicator
355

X-RAY IMAGE DATA MONITORING AND SIGNALING FOR PATIENT SAFETY

FIELD OF DISCLOSURE

The present disclosure relates to x-ray sensor systems, and more particularly, to x-ray image data monitoring and signaling for patient safety.

BACKGROUND

X-ray imaging is frequently used in dental care to visualize features of tooth anatomy, for example cavities or other defects that require attention and treatment. Originally, film was used to capture images generated by the relative attenuation of the x-ray radiation as it passed through different parts of the tooth. Later, electronic sensors came into use as a replacement for film and offered many advantages including faster access to the images (since the film development process was eliminated) and generally lower levels of radiation. Any level of x-ray radiation, however, is hazardous to the patient to some degree and it is generally desirable to avoid unnecessary radiation exposure whenever possible.

Although the following Detailed Description will proceed with reference being made to illustrative embodiments, many alternatives, modifications, and variations thereof will be apparent to those skilled in the art.

DETAILED DESCRIPTION

Techniques are provided for implementing an intraoral x-ray sensor system that can capture multiple dental x-ray images, each image associated with an x-ray pulse, and identify any image quality problems that arise, so that transmission of subsequent x-ray pulses can be terminated for increased patient safety. As noted previously, any level of x-ray radiation can be hazardous to some degree, and the effects are cumulative over time with multiple exposures, so it is beneficial to avoid unnecessary radiation exposure whenever possible. If it is determined that images generated from x-ray pulses are either too bright, too dark, or differ by at least a threshold value from previous images, (e.g., are underexposed or overexposed), then subjecting the patient to further x-ray pulses increases patient health risk because adequate diagnostic image results may not be obtained. To this end, and in accordance with an embodiment of the present disclosure, an x-ray sensor system is disclosed which provides detection of an unsatisfactory image and thus signals the x-ray system to terminate the x-ray exposure process, at least until corrections can be made, thereby decreasing total radiation and/or unnecessary radiation that a patient receives.

The disclosed techniques can be implemented in an intraoral sensor, for example, in a gate-level logic device, a microprocessor, an embedded processor, or a software product executable or otherwise controllable by such systems, although other embodiments will be apparent in light of this disclosure. In accordance with an embodiment, a methodology to implement these techniques includes integrating energy associated with a received x-ray pulse at an array of pixels. The method also includes multiplexing a readout of the integrated energy from the array of pixels, as analog signals, into channels, and performing analog to digital conversion of the analog signals of the channels into digital signals. The method further includes generating an error indicator in response to determining that a calculated mean of the digital signals is either greater than an upper threshold value associated with saturation, or less than a lower threshold value associated with underexposure. The method further includes transmitting the error indicator, or other suitable image quality data, over a Universal Serial Bus, to an imaging system that controls x-ray pulse transmission, to terminate transmission of further x-ray pulses.

It will be appreciated that the disclosed techniques for x-ray image data monitoring and signaling, as described herein, may provide improved patient safety, compared to existing imaging techniques that transmit a fixed number of x-ray pulses regardless of image quality. The advantages of the disclosed techniques are particularly important in the event of a malfunction in the x-ray pulse generator that results in the transmission of excessive radiation, which would be detected as an overexposure in an early image. The techniques disclosed herein may further be implemented in hardware or software or a combination thereof. Numerous embodiments and applications will be apparent in light of this disclosure.

Figure 1:
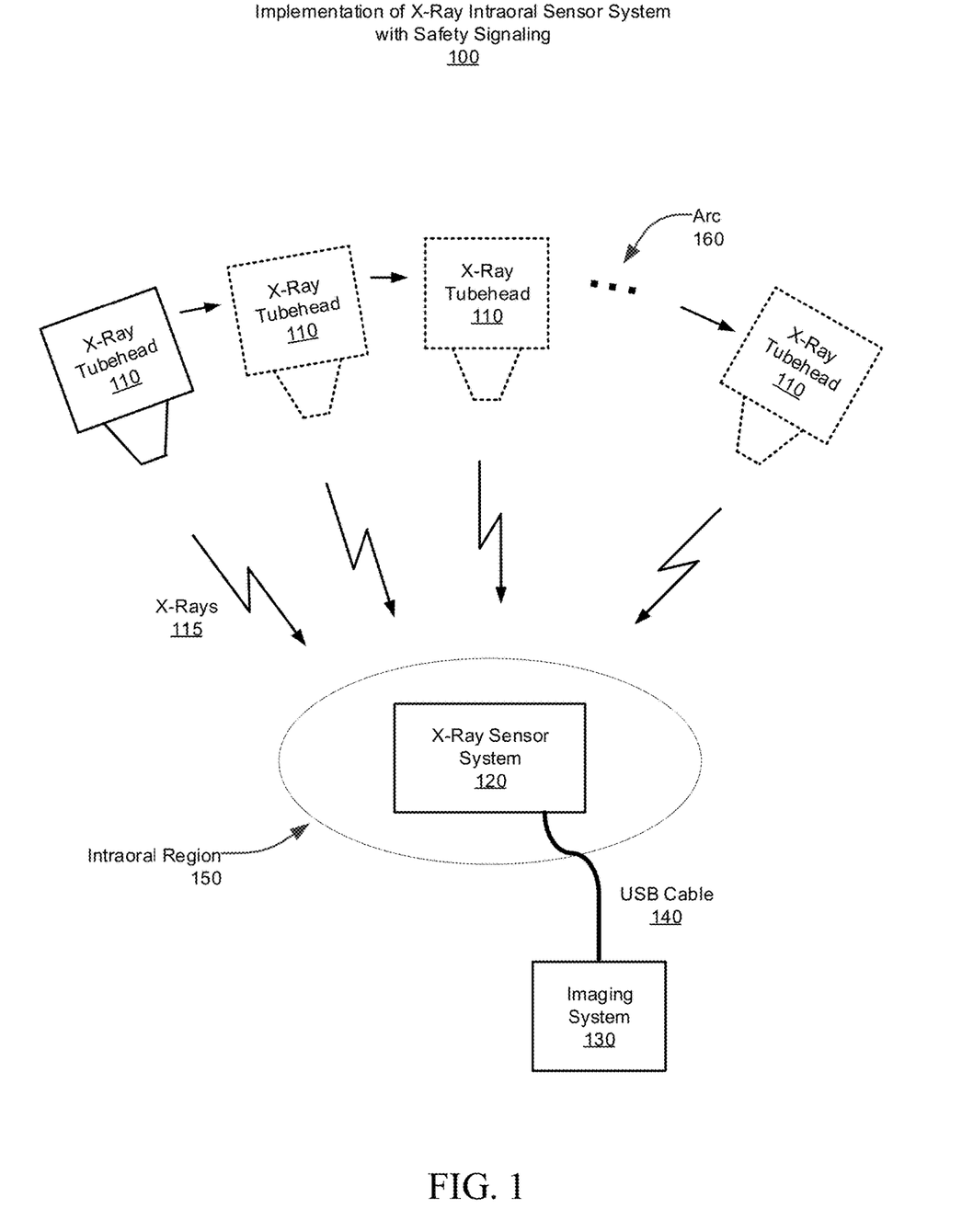
FIG. 1 illustrates an implementation of an x-ray sensor system with safety signaling, in accordance with an embodiment of the present disclosure.

FIG. 1 illustrates an implementation 100 of an x-ray sensor system 120 with safety signaling, in accordance with an embodiment of the present disclosure. An x-ray tubehead 110 generates x-rays 115 which are directed to the intraoral region of interest 150, for example the mouth of a patient undergoing dental imaging. The x-ray sensor system 120 is located in the intraoral region, for example behind a tooth being imaged, such that the x-rays 115 pass from the tubehead 110, through the tooth, before illuminating the sensor system 120. The sensor system then forms an image which is transmitted to an imaging system 130 which collects that image as one of multiple such images from varying angles. In some embodiments, the imaging system 130 may use the multiple images to perform tomographic processing to generate a 3-dimensional image. In some embodiments, the transmission may be over a cable, such as USB cable 140, which runs out of the patient's mouth, although other communications schemes are possible, including wireless communications.

In operation, the tubehead 110 travels through an arc 160 as shown and generates multiple x-ray pulses over the course of that range of travel. Each x-ray pulse may therefore illuminate the tooth from a different angle. For example, in some embodiments, 30 pulses are generated over 3 seconds of travel through a 40 degree arc. The x-ray sensor system 120 is configured to generate a 2-dimensional image for each x-ray pulse. In some embodiments, the imaging system 130 is configured to collect and tomographically combine the 2-dimensional images to generate a 3-dimensional image of the tooth that can provide greater diagnostic information to the dental practitioner than would otherwise be available from individual 2-dimensional images. In some embodiments, the x-ray sensor system 120 is also configured to generate an error indicator (or other data), in response to identification of an unsatisfactory image, as will be described in greater detail below. This indicator can be generated and transmitted relatively quickly to the imaging system 130 so that transmission of further x-ray pulses may be terminated to increase patient safety.

Figure 2:
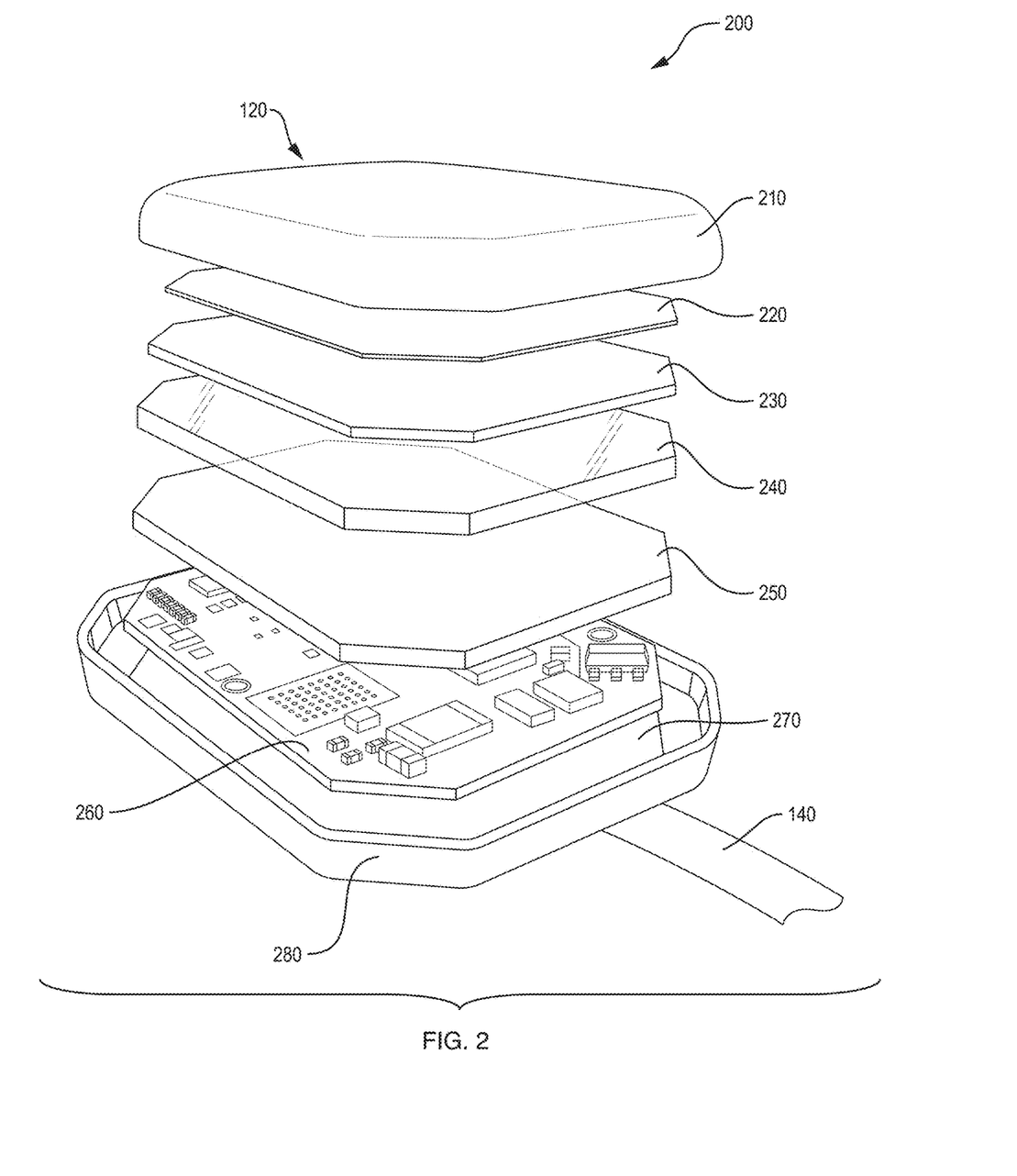
FIG. 2 is an exploded view of an example implementation of the x-ray sensor system of FIG. 1, configured in accordance with an embodiment of the present disclosure.

FIG. 2 is an exploded view 200 of an example implementation of the x-ray sensor system 120 of FIG. 1, configured in accordance with an embodiment of the present disclosure. The x-ray sensor system 120 is shown to comprise a number of layers including a buffer pad 220, a Cesium Iodide layer 230, a fiber optic plate 240, a Complementary Metal Oxide Semiconductor (CMOS) sensor die 250, a circuit board 260, and a metallization layer 270. The layers are enclosed in a capsule comprising a front, x-ray facing, portion 210, and a rear portion 280. The capsule provides a sealed and hygienic housing for the components/layers that is suitable for use as a dental intraoral device. Additional layers (not shown) may be included in some embodiments, for any suitable purpose.

The buffer pad 220 is configured to protect the Cesium Iodide layer, which is relatively fragile, and may also absorb stray light that reflects off the metallization layer. In some embodiments, the buffer pad may be fabricated as a layer of silicone, although any number of protective materials can be used (e.g., foam or plastic).

The Cesium Iodide layer 230 is configured to generate a fluorescent glow at a strength that depends on the level of x-ray illumination. In other words, a location on the Cesium Iodide layer that receives more x-ray radiation will glow more brightly than an area that receives less x-ray radiation. When the x-ray radiation passes through a tooth, the strength of the fluorescent glow will indicate the density of the tooth at that location (e.g., along the ray path of that portion of the x-ray). The Cesium Iodide layer 230 is a chemical coating that is disposed over the fiber optic plate 240. In addition to acting as a structural layer to support the Cesium Iodide, the fiber optic plate 240 also absorbs the x-ray radiation which protects the CMOS sensor die 250 and the circuit board 260 from damage.

The CMOS sensor die 250 comprises an array of photo diode circuits and is configured to detect the fluorescent glow generated by the Cesium Iodide layer 230. In some embodiments, each photo diode circuit generates an analog signal that may be associated with a pixel of the resultant x-ray image.

Figure 5:
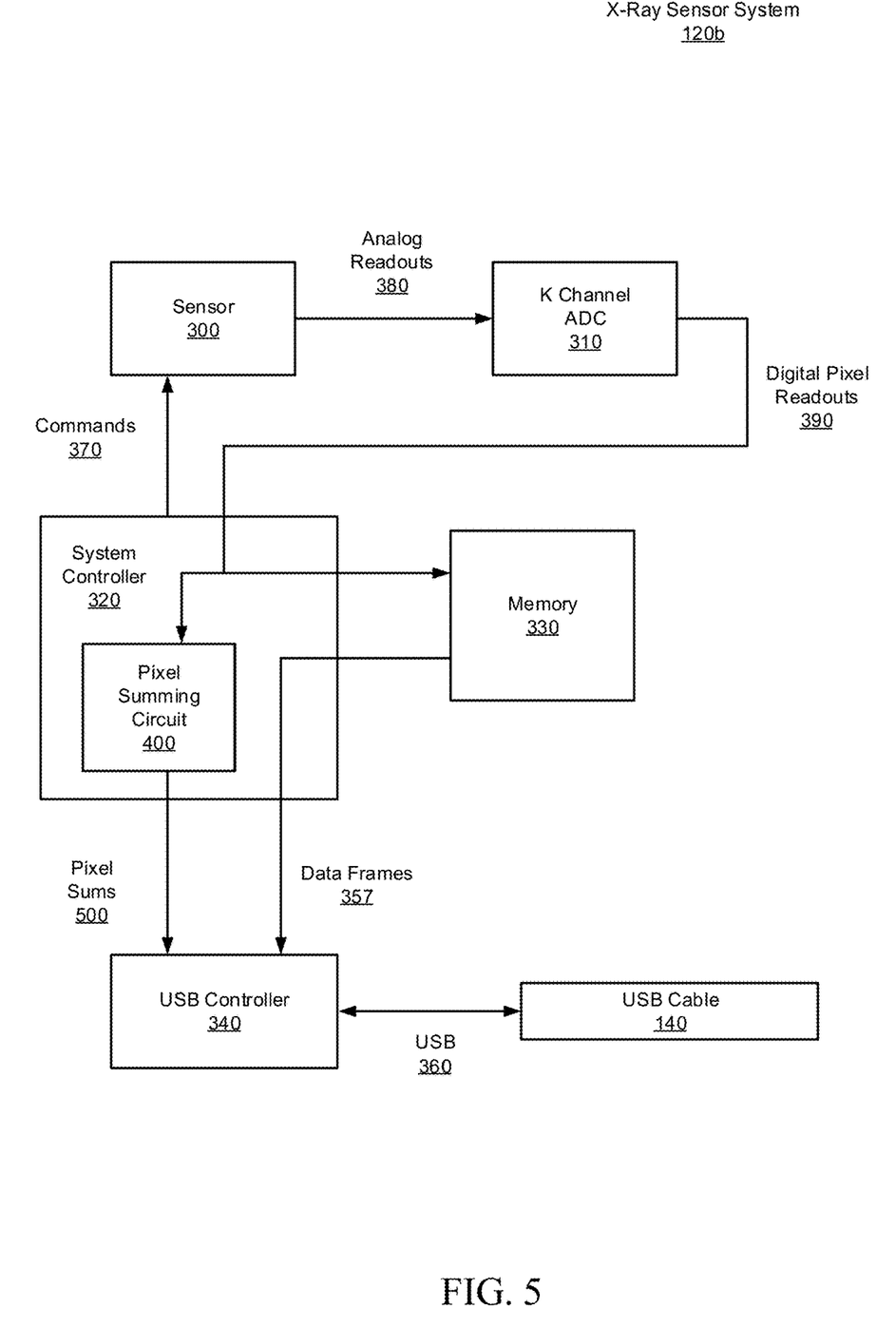
FIG. 5 is a block diagram of the x-ray sensor system of FIG. 1, configured in accordance with another embodiment of the present disclosure.

The circuit board 260 is configured to receive, process, store, and transmit the signals provided by the CMOS sensor die 250. Further details of sensor die 250 and circuit board 260 are discussed with respect to FIGS. 3 through 5. In particular, sensor die 250 may include a pixel array, and circuit board 260 may include ADC 310, system controller 320, memory 330, and USB controller 340 (FIGS. 3 and 5).

The metallization layer 270, which may include a layer of lead, is configured to provide radiation protection as a safety measure to prevent stray x-ray radiation from reaching the patient.

The x-ray sensor system 120 also includes a communication cable 140, which may be a USB cable in some embodiments, and is configured to provide collected x-ray sensor data and error indicator to the imaging system 130.

Figure 3:
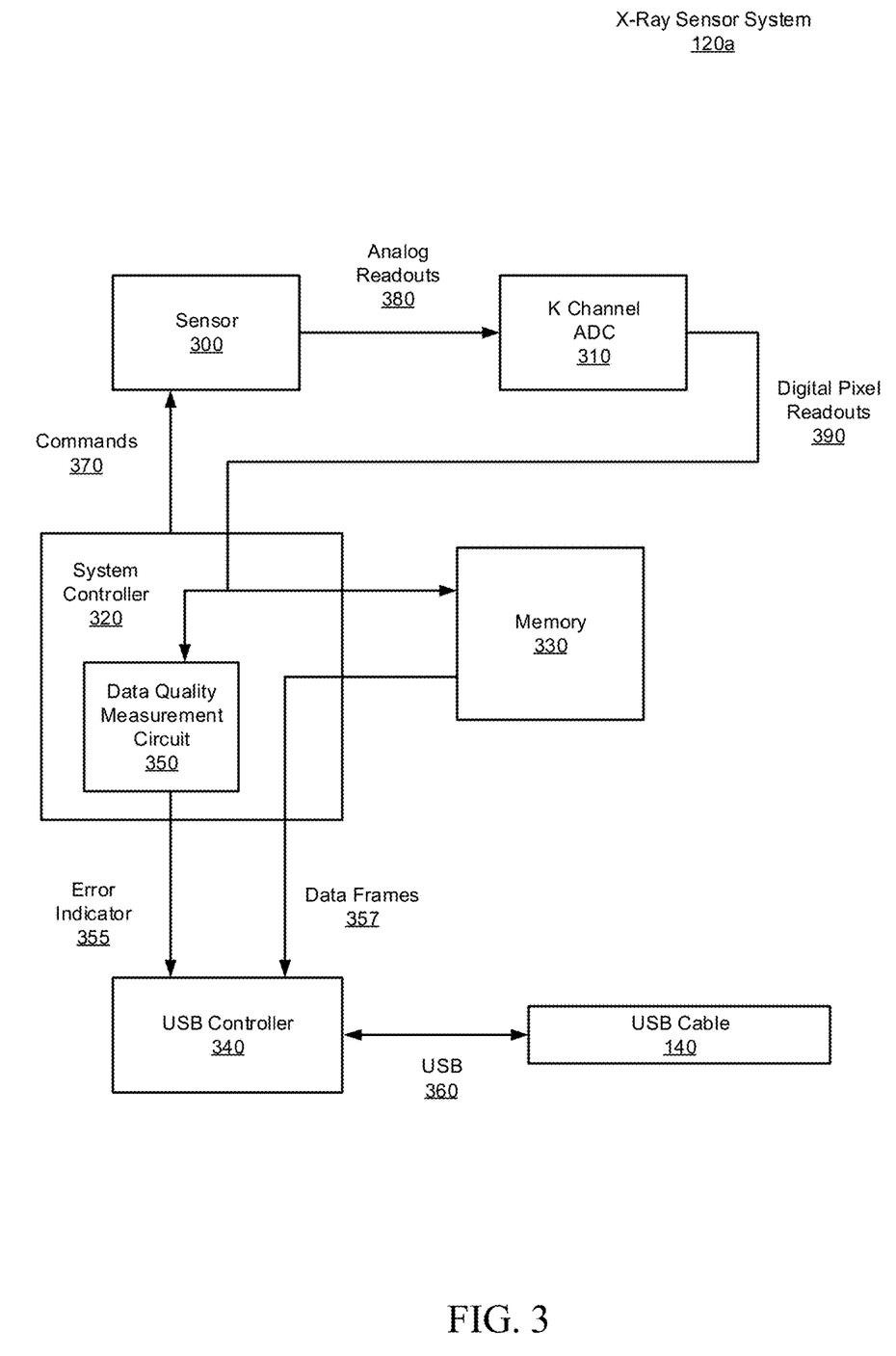
FIG. 3 is a block diagram of the x-ray sensor system of FIG. 1 and shows further details of the CMOS sensor die and circuit board of FIG. 2, configured in accordance with an embodiment of the present disclosure.

FIG. 3 is a block diagram of the x-ray sensor system 120 of FIG. 1, configured in accordance with an embodiment of the present disclosure. The x-ray sensor system 120a, of this embodiment, is shown to include a sensor 300, a multichannel analog to digital converter (ADC) 310, a system controller 320, which includes data quality measurement circuit 350, a memory 330, and a USB Controller 340.

The sensor 300 comprises an array of pixels (e.g., pixel circuits comprising photo diodes and associated circuitry). The sensor 300 is configured to capture energy associated with an x-ray pulse and provide an analog signal readout 380 of the energy from each pixel into multiplexed parallel channels (e.g., K channels).

The multichannel ADC 310 is configured to simultaneously convert, or otherwise perform parallel conversion of, the analog signals 380 of the K channels into digital signals 390. Thus, each analog signal 380 is received by a corresponding one of the channels of the multichannel ADC, according to some embodiments. In such a case, K analog signals 380 can be simultaneously converted to their digital equivalents 390. Note that, as used herein, simultaneous conversion is intended to include any form of contemporaneous or parallel conversion and is not intended to be limited to precise start and stop times for the processing of each channel. Rather, the processing of a given channel may overlap with the processing of the other channels, but some of the channels may finish processing before other channels finish; likewise, some of the channels may commence processing before other channels commence. So long as there is contemporaneous overlap of the processing, that processing may be considered to be simultaneous or parallel processing. Note that in some embodiments, K may be one so that only a single channel is implemented and operations are not performed in parallel.

The system controller 320 is configured to generate commands 370 to the sensor 300 to clear the sensor 300 of data from a previous x-ray pulse, start and stop data collection on a new x-ray pulse, and adjust the gain setting of the sensor photodiodes. The system controller 320 is also configured to control transfer of the digital pixel readouts 390 from the ADC 310 to the data quality measurement circuit 350 and to the memory 330. The system controller 320 is further configured to control transfer of data frames 357 (e.g., images made up of the digital pixel readouts 390) from the memory 330 to the USB controller 340.

The data quality measurement circuit 350 is configured to determine, for each x-ray pulse, the average of the integrated energy values that are read out from the pixels. An average value that is too low indicates that the associated image is underexposed while an average value that is too high indicates that the associated image is overexposed (or vice versa for negative images in which the polarity is reversed). In either case, there is likely no reason to transmit further x-ray pulses since the images will not be useful and the additional radiation is harmful to the patient. An error indicator 355 is generated, as will be explained below, to indicate that either condition (over/under exposure) is detected. In some embodiments, the data quality measurement circuit 350 is configured to generate the error indicator 355 in response to determining that the average value is differs from previously computed average values (from prior x-ray pulses) by more than a threshold percentage. In some embodiments, median filtering (or other non-linear filtering) may be applied to the integrated energy values that are read out from the pixels prior to performing the averaging.

The USB Controller 340 is configured to transmit the error indicator 355 and the data frames 357 to the imaging system 130, for example over the USB bus 360. In some embodiments, the error indicator 355 is transmitted over a USB control endpoint (e.g., in response to a request by the imaging system 130) or a USB interrupt endpoint, and the data frames 357 are transmitted over a USB bulk endpoint.

Figure 4:
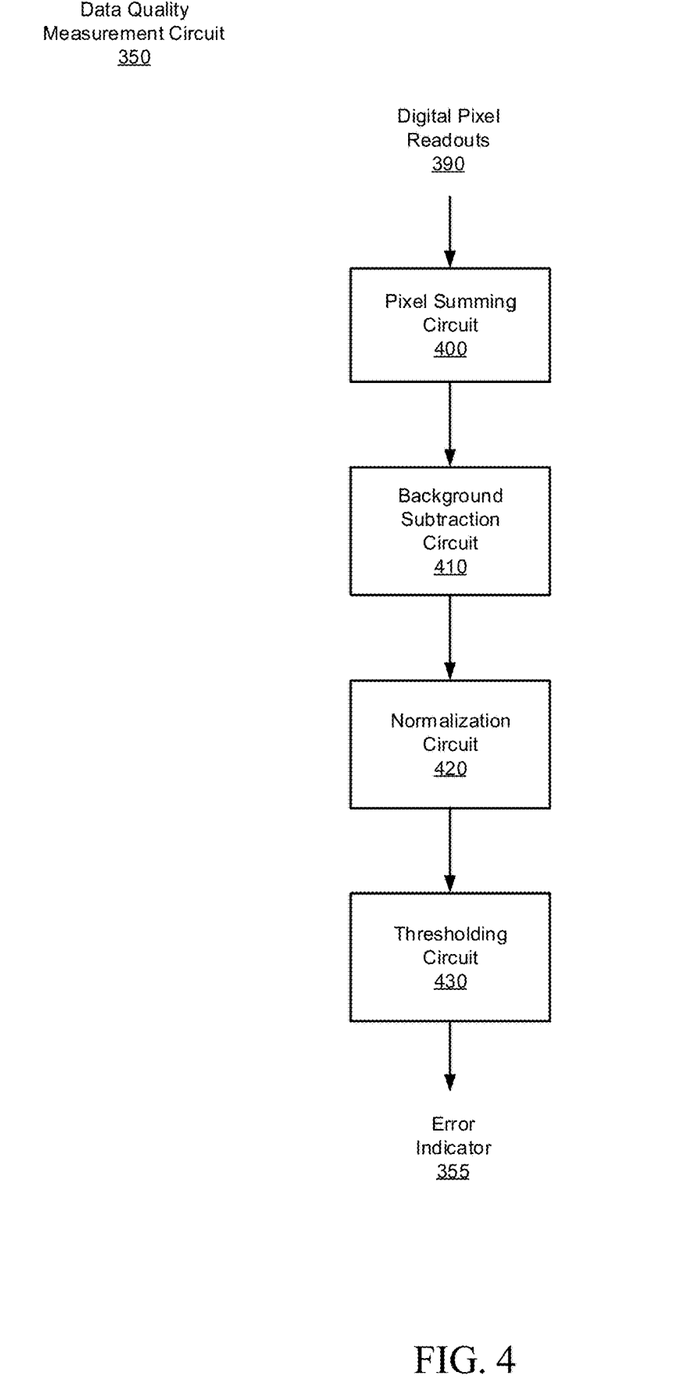
FIG. 4 is a detailed block diagram of the data quality measurement circuit of the system controller of FIG. 3, configured in accordance with an embodiment of the present disclosure.

FIG. 4 is a detailed block diagram of the data quality measurement circuit 350 of the system controller of FIG. 3, configured in accordance with an embodiment of the present disclosure. The data quality measurement circuit 350 is shown to include a pixel summing circuit 400, a background subtraction circuit 410, a normalization circuit 420, and a thresholding circuit 430.

The pixel summing circuit 400 is configured to sum the data values provided by all active pixels of the pixel array, for example in the digital pixel readouts 390. In some embodiments, the pixel summing circuit may be implemented as K individual accumulators, one for each of the K ADC channels, the outputs of which are then summed by a final accumulator.

The background subtraction circuit 410 is configured to subtract the quiescent background level (also referred to as dark background) from the sum. The dark background level is the energy produced by the pixels when no x-ray radiation is present.

The normalization circuit 420 is configured to divide the sum (after subtraction of the background level) by the number of active pixels of the array to calculate a mean or average energy value that was generated by the pixel array in response to the x-ray pulse.

The thresholding circuit 430 is configured to compare that mean energy level to an upper and lower threshold. The upper threshold is associated with an overexposed image and the lower threshold is associated with an underexposed image. If the mean energy level lies outside of that range (e.g., greater then the upper threshold or less than the lower threshold), then an error indicator 355 is generated. In some embodiments, the thresholds may include offsets to compensate for an expected dark background level so that the background subtraction process may be omitted.

FIG. 5 is a block diagram of the x-ray sensor system 120 of FIG. 1, configured in accordance with another embodiment of the present disclosure. The x-ray sensor system 120b, of this embodiment, is shown to include the sensor 300, the multichannel analog to digital converter (ADC) 310, the system controller 320, the memory 330, and the USB Controller 340, as previously shown for embodiment 120a. The difference between this embodiment 120b and the previous embodiment 120a is that the data quality measurement circuit 350 is replaced by the pixel summing circuit 400. As such, the pixel sums 500 are generated and provided to the imaging system 130 rather than the error indicator 355. In this embodiment, the task of determining whether or not an error has occurred is shifted to the imaging system 130, which does so based on the provided pixel sums 500. In some embodiment, the pixel sum may be a single value representing the sum of all pixels, while in other embodiments, K separate pixels sums, or partial sums (one for each ADC channel), may be transmitted to the imaging system.

Figure 6:
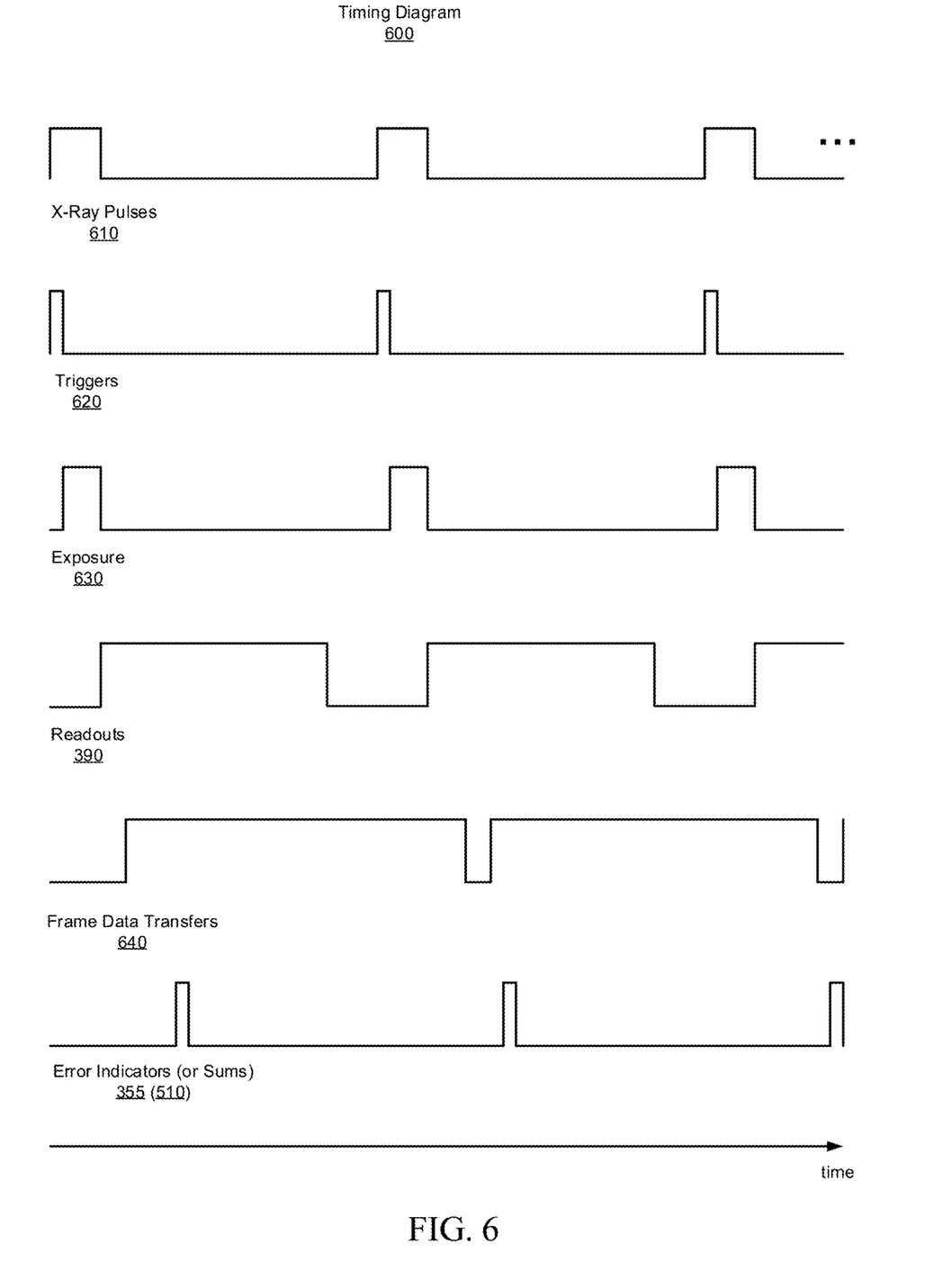
FIG. 6 is a timing diagram of the safety signaling operation of the x-ray sensor system of FIGS. 3 and 5, in accordance with an embodiment of the present disclosure.

FIG. 6 is a timing diagram 600 of the operation of the x-ray sensor system of FIGS. 3 and 5, in accordance with an embodiment of the present disclosure. A series of x-ray pulses 610 are shown along the top timeline. In some embodiments, 30 pulses are generated and received over a course of 3 seconds, which is to say that 10 pulses per second are processed by the sensor system 120 and that up to 30 images may be stored in memory prior to transmission from the sensor to the imaging system. A trigger 620 is provided (e.g., by the imaging system) at the beginning of each x-ray pulse so that the sensor is triggered to start integrating energy for that pulse. The integration period may be referred to as an exposure 630. In some embodiments, the exposure may last for approximately 32 msec.

A frame of data is then read out from the sensor 300 to the memory 330 during the readout time period 390. In some embodiments, the frame readout time period 390 may be approximately 67 msec and so the readout may be finishing just before the next x-ray pulse is transmitted, although the illustration in FIG. 6 shows an example having a longer time gap between readout and the next pulse.

The process 640, of transferring the data frames 357 to the imaging system, may begin at any time after the readout starts and data is available in memory 330 to transfer. As shown, the data transfer may take a significant period of time and may not complete until after the next x-ray pulse begins. If the transfer continues to fall behind, it may eventually be several frames behind the most recent (e.g., current) exposure.

The error indicator 355 (or sums or partial sums 510) can be computed and made available for transfer as soon as the readout 390 is completed. In some embodiments, the indicator 355 may be available before the readout 390 is completed, if the indicator is based on a portion of the readout data, for example a sum of 75% of the pixels to be read out. Since the indicator 355 (or sums 510) is represented by a single data value (or small number K of data values, in the case of sums per channel), the transfer to the imaging system can be completed relatively quickly, as shown. This allows the imaging system to terminate the x-ray pulses, if appropriate, before the next pulse is transmitted, rather than having to wait for this frame data transfer, which as noted above can run one or more frames behind the current exposure and thus subject the patient to unnecessary radiation.

The process then repeats for each subsequent x-ray pulse until the series is completed or terminated due to detection of an error condition.

Methodology

Figure 7:
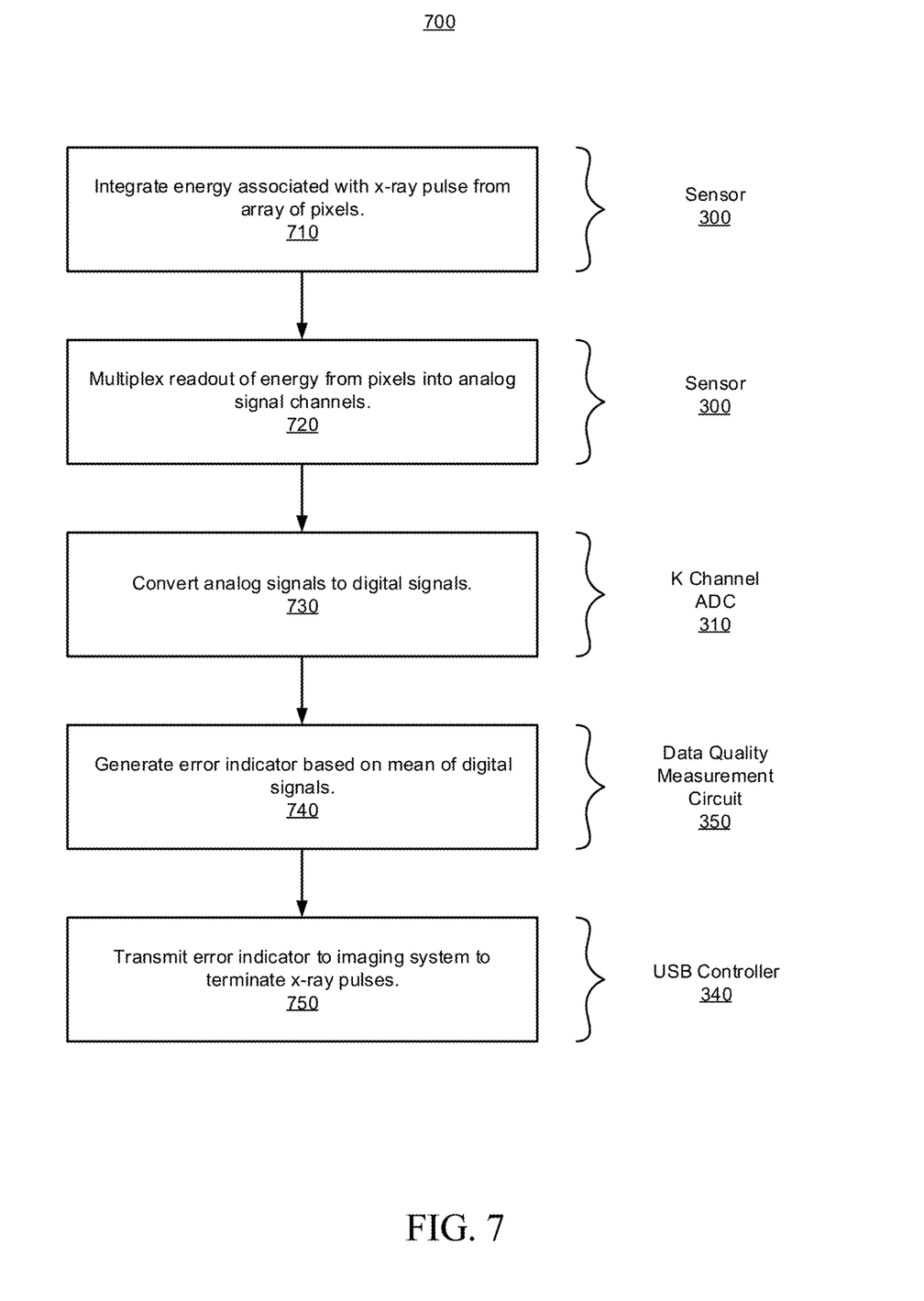
FIG. 7 is a flowchart illustrating a methodology for operation of the x-ray sensor system, in accordance with an embodiment of the present disclosure.

FIG. 7 is a flowchart illustrating a methodology 700 for operation of the x-ray sensor system with safety signaling, in accordance with an embodiment of the present disclosure. As can be seen, the example method includes a number of phases and sub-processes, the sequence of which may vary from one embodiment to another. However, when considered in the aggregate, these phases and sub-processes form a process for x-ray sensing with safety signaling, in accordance with certain of the embodiments disclosed herein. These embodiments can be implemented, for example using the system architecture illustrated in FIGS. 1-6, as described above. However other system architectures can be used in other embodiments, as will be apparent in light of this disclosure. To this end, the correlation of the various functions shown in FIG. 7 to the specific components illustrated in FIGS. 1-6, is not intended to imply any structural and/or use limitations. Rather other embodiments may include, for example, varying degrees of integration wherein multiple functionalities are effectively performed by one system. Numerous variations and alternative configurations will be apparent in light of this disclosure.

As illustrated in FIG. 7, in one embodiment method 700 commences, at operation 710, by integrating energy associated with a received x-ray pulse at an array of pixels.

Next, at operation 720, a readout of the integrated energy from the array of pixels is multiplexed, as analog signals, into two or more channels.

At operation 730, analog to digital conversion is performed on the analog signals of the channels to generate digital signals.

At operation 740, an error indicator is generated in response to determining that a calculated mean of the digital signals is either greater than an upper threshold value associated with saturation or less than a lower threshold value associated with underexposure.

At operation 750, the error indicator is transmitted over a USB, to an imaging system, to terminate transmission of further x-ray pulses. In some embodiments, the error indicator is transmitted through a USB control endpoint or a USB interrupt endpoint, and the transmission occurs prior to reception of a subsequent x-ray pulse.

Of course, in some embodiments, additional operations may be performed, as previously described in connection with the system. These additional operations may include, for example, calculating the mean by summing the digital signals, subtracting a dark background offset value from the sum, and dividing by a count of active pixels in the array of pixels. In some embodiments, the mean or the sum is transmitted to the imaging system, either in addition to the error indicator, or in place of the error indicator.

Example Systems

Figure 8:
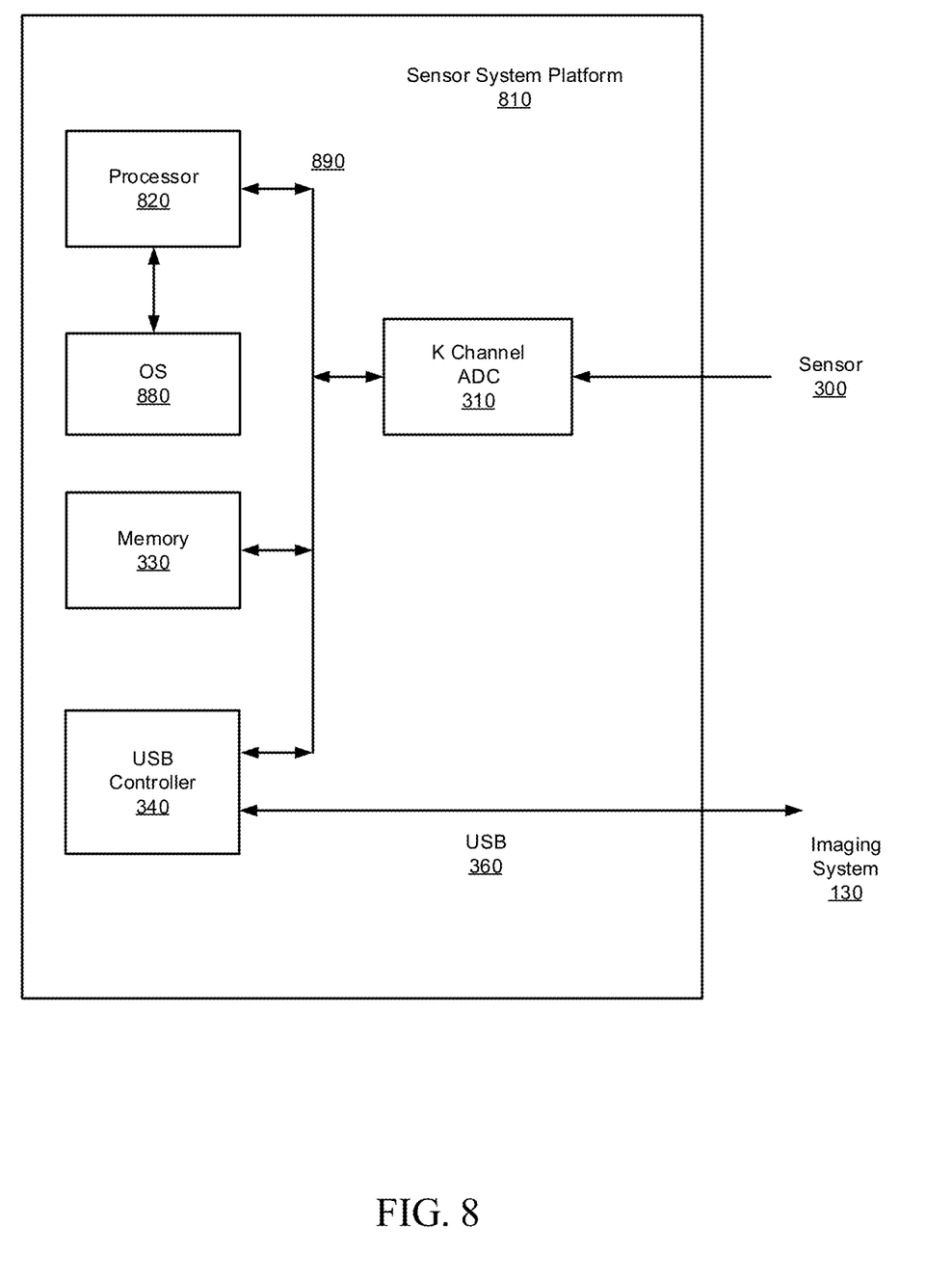
FIG. 8 is a block diagram schematically illustrating a platform for the x-ray sensor system, in accordance with certain embodiments of the present disclosure.

FIG. 8 is a block diagram schematically illustrating a platform 810 for the x-ray sensor system, in accordance with certain embodiments of the present disclosure. In some embodiments, the sensor system platform 810, or portions thereof, may be hosted on, or otherwise be incorporated onto a circuit board configured to fit in a capsule 210, 280 that is suitable for use as an intraoral dental device.

In some embodiments, platform 810 may comprise any combination of a processor 820, a memory 330, a USB controller 340 (or other suitable communication interface), and multichannel ADC 310. As can be further seen, a bus 890 is also provided to allow for communication between the various components listed above and/or other components not shown. Other componentry and functionality not reflected in the block diagram of FIG. 8 will be apparent in light of this disclosure, and it will be appreciated that other embodiments are not limited to any particular hardware configuration.

Processor 820 can be any suitable processor, and may include one or more coprocessors or controllers, such as an audio processor, a graphics processing unit, or hardware accelerator, to assist in control and processing operations associated with sensor system of platform 810. In some embodiments, the processor 820 may be implemented as any number of processor cores. The processor (or processor cores) may be any type of processor, such as, for example, a microprocessor, an embedded processor, a digital signal processor (DSP), a graphics processor (GPU), a network processor, a field programmable gate array or other device configured to execute code. The processors may be multi-threaded cores in that they may include more than one hardware thread context (or "logical processor") per core. Processor 820 may be implemented as a complex instruction set computer (CISC) or a reduced instruction set computer (RISC) processor.

Memory 330 can be implemented using any suitable type of digital storage including, for example, flash memory and/or random access memory (RAM). In some embodiments, the memory 330 may include various layers of memory hierarchy and/or memory caches as are known to those of skill in the art. Memory 330 may be implemented as a volatile memory device such as, but not limited to, a RAM, dynamic RAM (DRAM), or static RAM (SRAM) device.

Processor 820 may be configured to execute an Operating System (OS) 880 which may comprise any suitable operating system, such as Google Android (Google Inc., Mountain View, CA), Microsoft Windows (Microsoft Corp., Redmond, WA), Apple OS X (Apple Inc., Cupertino, CA), Linux, or a real-time operating system (RTOS). As will be appreciated in light of this disclosure, the techniques provided herein can be implemented without regard to the particular operating system provided in conjunction with sensor system platform 810, and therefore may also be implemented using any suitable existing or subsequently-developed systems or platforms.

It will be appreciated that in some embodiments, some of the various components of sensor system platform 810 may be combined or integrated in a system-on-a-chip (SoC) architecture. In some embodiments, the components may be hardware components, firmware components, software components or any suitable combination of hardware, firmware or software.

Processor 820, which may be implemented as an FPGA in some embodiments, is configured to perform the functions of controller 320, as described previously.

Various embodiments of sensor system platform 810 may be implemented using hardware elements, software elements, or a combination of both. Examples of hardware elements may include processors, microprocessors, circuits, circuit elements (for example, transistors, resistors, capacitors, inductors, and so forth), integrated circuits, application-specific integrated circuits (ASICs, or other purpose-built semiconductors), programmable logic devices, digital signal processors, field programmable gate arrays (FPGAs), logic gates, registers, semiconductor devices, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power level, heat tolerances, processing cycle budget, input data rates, output data rates, memory resources, data bus speeds, and other design or performance constraints.

The various embodiments disclosed herein can be implemented in various forms of hardware, software, firmware, and/or special purpose processors. For example, in one embodiment at least one non-transitory computer readable storage medium has instructions encoded thereon that, when executed by one or more processors, causes one or more of the methodologies disclosed herein to be implemented. Other componentry and functionality not reflected in the illustrations will be apparent in light of this disclosure, and it will be appreciated that other embodiments are not limited to any particular hardware or software configuration. Thus, in other embodiments sensor system platform 810 may comprise additional, fewer, or alternative subcomponents as compared to those included in the example embodiment of FIG. 8.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still cooperate or interact with each other.

The aforementioned non-transitory computer readable medium may be any suitable medium for storing digital information, such as a hard drive, a server, a flash memory, and/or random access memory (RAM), or a combination of memories. In alternative embodiments, the components and/or modules disclosed herein can be implemented with hardware, including gate-level logic such as a field-programmable gate array (FPGA), or alternatively, a purpose-built semiconductor such as an application-specific integrated circuit (ASIC). In some embodiments, the hardware may be modeled or developed using hardware description languages such as, for example Verilog or VHDL. Still other embodiments may be implemented with a microcontroller having a number of input/output ports for receiving and outputting data, and a number of embedded routines for carrying out the various functionalities disclosed herein. It will be apparent that any suitable combination of hardware, software, and firmware can be used, and that other embodiments are not limited to any particular system architecture.

Some examples may be implemented, for example, using a machine-readable medium or article which may store an instruction or a set of instructions that, if executed by a machine, may cause the machine to perform a method and/or operations in accordance with an embodiment provided herein. Such a machine may include, for example, any suitable processing platform, computing platform, computing device, processing device, computing system, processing system, computer, process, or the like, and may be implemented using any suitable combination of hardware and/or software. The machine-readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CD-RW) memory, optical disk, magnetic media, magneto-optical media, removable memory cards or disks, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing," "computing," "calculating," "determining," or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

The terms "circuit" or "circuitry," as used in any embodiment herein, are functional structures that include hardware, or a combination of hardware and software, and may comprise, for example, singly or in any combination, hardwired circuitry, programmable circuitry such as computer processors comprising one or more individual instruction processing cores, state machine circuitry, and/or gate level logic. The circuitry may include a processor and/or controller programmed or otherwise configured to execute one or more instructions to perform one or more operations described herein. The instructions may be embodied as, for example, an application, software, firmware, or one or more embedded routines configured to cause the circuitry to perform any of the aforementioned operations. Software may be embodied as a software package, code, instructions, instruction sets and/or data recorded on a computer-readable storage device. Software may be embodied or implemented to include any number of processes, and processes, in turn, may be embodied or implemented to include any number of threads or parallel processes in a hierarchical fashion. Firmware may be embodied as code, instructions or instruction sets and/or data that are hard-coded (e.g., nonvolatile) in memory devices. The circuitry may, collectively or individually, be embodied as circuitry that forms part of a larger system, for example, an integrated circuit (IC), an application-specific integrated circuit (ASIC), a system-on-a-chip (SoC), computers, and other processor-based or functional systems. Other embodiments may be implemented as software executed by a programmable device. In any such hardware cases that include executable software, the terms "circuit" or "circuitry" are intended to include a combination of software and hardware such as a programmable device or a processor capable of executing the software. As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Numerous specific details have been set forth herein to provide a thorough understanding of the embodiments. It will be understood by an ordinarily-skilled artisan, however, that the embodiments may be practiced without these specific details. In other instances, well known operations, components, and circuits have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments The following examples pertain to further embodiments, from which numerous permutations and configurations will be apparent.

One example embodiment of the present disclosure provides an intraoral x-ray sensor safety system comprising: an array of pixels configured to integrate energy associated with a received x-ray pulse; a multiplexer configured to readout the integrated energy from the array of pixels, as analog signals, into two or more channels; two or more analog to digital converter (ADC) circuits configured to perform conversion of the analog signals of the channels into digital signals, such that each ADC receives the analog signal of a corresponding one of the channels; and a data quality measurement circuit configured to generate an error indicator in response to determining that a calculated mean of the digital signals is either greater than an upper threshold value or less than a lower threshold value.

In some cases, the data quality measurement circuit is configured to calculate the mean by summing the digital signals, subtracting a dark background offset value from the sum, and dividing by a count of active pixels in the array of pixels. In some cases, the data quality measurement circuit is configured to generate the error indicator in response to determining that the calculated mean differs from a previously calculated mean by more than a threshold percentage. In some cases, the system further comprises a Universal Serial Bus (USB) controller configured to transmit the error indicator over a USB, to an imaging system, to terminate transmission of further x-ray pulses. In some such cases, the error indicator is transmitted through a control endpoint of the USB controller or an interrupt endpoint of the USB controller. In some such cases, the USB controller is configured to transmit the error indicator prior to reception of a subsequent x-ray pulse. In some such cases, the USB controller is configured to transmit the calculated mean to the imaging system through a control endpoint of the USB controller or an interrupt endpoint of the USB controller. In some such cases, the USB controller is configured to transmit frames of data to the imaging system through a bulk endpoint of the USB controller, the frames of data comprising the digital signals. In some cases, the upper threshold value corresponds to a saturated image and the lower threshold value corresponds to an underexposed image.

Another example embodiment of the present disclosure provides a computer program product including one or more non-transitory machine-readable mediums encoded with instructions that when executed by one or more processors cause a process to be carried out for intraoral x-ray safety signaling, the process comprising: integrating energy associated with a received x-ray pulse at an array of pixels; multiplexing a readout of the integrated energy from the array of pixels, as analog signals, into two or more channels; performing analog to digital conversion of the analog signals of the channels into digital signals; and generating an error indicator in response to determining that a calculated mean of the digital signals is either greater than an upper threshold value or less than a lower threshold value.

In some cases, the process further comprises calculating the mean by summing the digital signals, subtracting a dark background offset value from the sum, and dividing by a count of active pixels in the array of pixels. In some such cases, the process further comprises transmitting the error indicator over a Universal Serial Bus (USB), to an imaging system, to terminate transmission of further x-ray pulses. In some such cases, the process further comprises transmitting the error indicator through a USB control endpoint or a USB interrupt endpoint. In some such cases, the process further comprises transmitting the error indicator prior to reception of a subsequent x-ray pulse. In some such cases, the process further comprises transmitting the calculated mean to the imaging system through a USB control endpoint or a USB interrupt endpoint. In some such cases, the process further comprises transmitting frames of data to the imaging system through a USB bulk endpoint, the frames of data comprising the digital signals. In some cases, the upper threshold value corresponds to a saturated image and the lower threshold value corresponds to an underexposed image.

Another example embodiment of the present disclosure provides an intraoral x-ray sensor safety system comprising: an array of pixels configured to integrate energy associated with a received x-ray pulse; a multiplexer configured to readout the integrated energy from the array of pixels, as analog signals, into two or more channels; two or more analog to digital converter (ADC) circuits configured to perform conversion of the analog signals of the channels into digital signals, such that each ADC receives the analog signal of a corresponding one of the channels; a summing circuit configured to generate a sum of the digital signals; and a Universal Serial Bus (USB) controller configured to transmit the sum over a USB, to an imaging system, to determine whether to terminate transmission of further x-ray pulses.

In some cases, the USB controller is configured to transmit the sum prior to reception of a subsequent x-ray pulse. In some such cases, the USB controller is configured to transmit the sum through a control endpoint of the USB controller or an interrupt endpoint of the USB controller and to transmit frames of data to the imaging system through a bulk endpoint of the USB controller, the frames of data comprising the digital signals.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. It is intended that the scope of the present disclosure be limited not by this detailed description, but rather by the claims appended hereto. Future filed applications claiming priority to this application may claim the disclosed subject matter in a different manner and may generally include any set of one or more elements as variously disclosed or otherwise demonstrated herein.

What is claimed is:

1. An intraoral x-ray sensor safety system comprising:
   an array of pixels configured to integrate energy associated with a received x-ray pulse;
   a multiplexer configured to readout the integrated energy from the array of pixels, as analog signals, into two or more channels;

two or more analog to digital converter (ADC) circuits configured to perform conversion of the analog signals of the channels into digital signals, such that each ADC receives the analog signal of a corresponding one of the channels;

a data quality measurement circuit configured to generate an error indicator in response to determining that a calculated mean of the digital signals is either greater than an upper threshold value or less than a lower threshold value, wherein the data quality measurement circuit is configured to calculate the mean by summing the digital signals, subtracting a dark background offset value from the sum, and dividing by a count of active pixels in the array of pixels.

2. The system of claim 1, wherein the data quality measurement circuit is configured to generate the error indicator in response to determining that the calculated mean differs from a previously calculated mean by more than a threshold percentage.

3. The system of claim 1, further comprising a Universal Serial Bus (USB) controller configured to transmit the error indicator over a USB, to an imaging system, to terminate transmission of further x-ray pulses.

4. The system of claim 3, wherein the error indicator is transmitted through a control endpoint of the USB controller or an interrupt endpoint of the USB controller.

5. The system of claim 3, wherein the USB controller is configured to transmit the error indicator prior to reception of a subsequent x-ray pulse.

6. The system of claim 3, wherein the USB controller is configured to transmit the calculated mean to the imaging system through a control endpoint of the USB controller or an interrupt endpoint of the USB controller.

7. The system of claim 3, wherein the USB controller is configured to transmit the digital signals to the imaging system through a bulk endpoint of the USB controller.

8. The system of claim 1, wherein the upper threshold value corresponds to a saturated image and the lower threshold value corresponds to an underexposed image.

9. A computer program product including one or more non-transitory machine-readable mediums encoded with instructions that when executed by one or more processors cause a process to be carried out for intraoral x-ray safety signaling, the process comprising:

integrating energy associated with a received x-ray pulse at an array of pixels;

multiplexing a readout of the integrated energy from the array of pixels, as analog signals, into two or more channels;

performing analog to digital conversion of the analog signals of the channels into digital signals; and generating an error indicator in response to determining that a calculated mean of the digital signals is either greater than an upper threshold value or less than a lower threshold value; and calculating the mean by summing the digital signals, subtracting a dark background offset value from the sum, and dividing by a count of active pixels in the array of pixels.

10. The computer program product of claim 9, wherein the process further comprises transmitting the error indicator over a Universal Serial Bus (USB), to an imaging system, to terminate transmission of further x-ray pulses.

11. The computer program product of claim 10, wherein the process further comprises transmitting the error indicator through a USB control endpoint or a USB interrupt endpoint.

12. The computer program product of claim 10, wherein the process further comprises transmitting the error indicator prior to reception of a subsequent x-ray pulse.

13. The computer program product of claim 10, wherein the process further comprises transmitting the calculated mean to the imaging system through a USB control endpoint or a USB interrupt endpoint.

14. The computer program product of claim 10, wherein the process further comprises transmitting the digital signals to the imaging system through a USB bulk endpoint.

15. The computer program product of claim 9, wherein the upper threshold value corresponds to a saturated image and the lower threshold value corresponds to an underexposed image.

16. An intraoral x-ray sensor safety system comprising:
an array of pixels configured to integrate energy associated with a received x-ray pulse;
a multiplexer configured to readout the integrated energy from the array of pixels, as analog signals, into two or more channels;
two or more analog to digital converter (ADC) circuits configured to perform conversion of the analog signals of the channels into digital signals, such that each ADC receives the analog signal of a corresponding one of the channels;
a data quality measurement circuit configured to generate an error indicator in response to determining that a calculated mean of the digital signals is either greater than an upper threshold value or less than a lower threshold value,
wherein the data quality measurement circuit is configured to calculate the mean by summing the digital signals, subtracting a dark background offset value from the sum, and dividing by a count of active pixels in the array of pixels; and
a Universal Serial Bus (USB) controller configured to transmit the sum over a USB, to an imaging system, to determine whether to terminate transmission of further x-ray pulses.

17. The system of claim 16, wherein the USB controller is configured to transmit the sum prior to reception of a subsequent x-ray pulse.

18. The system of claim 16, wherein the USB controller is configured to transmit the sum through a control endpoint of the USB controller or an interrupt endpoint of the USB controller and to transmit frames the digital signals to the imaging system through a bulk endpoint of the USB controller.

* * * * *